(12) United States Patent
Chiarello et al.

(10) Patent No.: US 7,183,405 B2
(45) Date of Patent: Feb. 27, 2007

(54) COMPOSITIONS AND METHODS FOR LABELING OLIGONUCLEOTIDES

(75) Inventors: Ronald H. Chiarello, Castro Valley, CA (US); Wing-Cheong Liu, Belmont, CA (US); Gabriel G. Alvarado, San Mateo, CA (US)

(73) Assignee: Syn Gen, Inc., San Carlos, CA (US)

( * ) Notice: Subject to any disclaimer, the term of this patent is extended or adjusted under 35 U.S.C. 154(b) by 0 days.

(21) Appl. No.: 09/894,423

(22) Filed: Jun. 28, 2001

(65) Prior Publication Data

US 2003/0104380 A1    Jun. 5, 2003
US 2004/0234957 A9    Nov. 25, 2004

Related U.S. Application Data

(63) Continuation-in-part of application No. 09/344,226, filed on Jun. 25, 1999, now Pat. No. 6,750,357.

(51) Int. Cl.
    C07H 21/00        (2006.01)
(52) U.S. Cl. ..................................... 536/25.3
(58) Field of Classification Search ............... 536/25.3, 536/25.32
    See application file for complete search history.

(56) References Cited

U.S. PATENT DOCUMENTS

| | | | |
|---|---|---|---|
| 4,415,732 A | 11/1983 | Caruthers et al. | 536/27 |
| 4,500,707 A | 2/1985 | Caruthers et al. | 536/27 |
| 4,668,777 A | 5/1987 | Caruthers et al. | 536/27 |
| 4,683,195 A | 7/1987 | Mullis et al. | 435/6 |
| 4,683,202 A | 7/1987 | Mullis et al. | 435/91 |
| 4,762,779 A * | 8/1988 | Snitman | |
| 4,973,679 A | 11/1990 | Caruthers et al. | 536/27 |
| 5,218,103 A | 6/1993 | Caruthers et al. | 536/25.33 |
| 5,231,191 A | 7/1993 | Woo et al. | 549/220 |
| 5,278,302 A | 1/1994 | Caruthers et al. | 536/24.5 |
| 5,453,496 A | 9/1995 | Caruthers et al. | 536/24.5 |
| 6,255,476 B1 * | 7/2001 | Vinayak et al. | |

OTHER PUBLICATIONS

Caruthers et al., "Chemical Synthesis of Deoxyoligonucleotides by the Phosphoramidite Method," *Methods in Enzymology* 154:287-313 (1987).
Doty et al., "Strand Separation and Specific Recombination in Deoxyribonucleic Acids: Physical Chemicals Studies," *Proc. Natl. Acad. Sci. USA* 46:461 (1960).
Horvath et al., "An Automated DNA Synthesizer Employing Deoxynucleoside 3'-Phosphoramidites," *Methods in Enzymology* 154:314-326 (1987).
Hung et al., "Energy Transfer Primers with 5- or 6-Carboxyrhodamine-6G as Acceptor Chromophores," *Analytical Biochem.*, 238, 165-170, (1996).
Igloi, "Stratedies for introducing non-radioactive labels during the automated sequence analysis of necleic acids," *ELB Electronic Journal of Biotechnology* 1(1):1-8 (1998).
Jang et al., "Ligation mediated fluorescent labeling of DNA sequencing primers," *Nucleic Acids Research* 25(4):922-923 (1997).
Joslin Diabetes Center, DNA Core Facility, "DNA Stnthesis Steps," Revised Sep. 10, 1999 dnacore.joslab.harvard.edu/core/cycle.html.
Lyttle et al., "Versatile Linker Chemistry for Synthesis of 3'-Modified DNA," *Bioconjugate Chem* 8:193-198 (1997).
Marmur and Lane, "Strand Separation and Specific Recombination in Deoxyribonucleic Acids: Biological Studies," *Proc. Natl. Acad. Sci. USA* 46:453-461 (1960).
Paladichuk, "Fishing in a Molecular Sea," *The Scientist* 13(2):19 (1999), www.the-scientist.com/yr1999/jan/profile1_990118.html.
Pon, "Tips for Oligonucleotide Synthesis," www.abrf.org/ABRFNews/1994/December1994/dec94ponoligo.html.
Rios, "Phosphoramidite Chemistry," sonhouse.hunter.cuny.edu/facilities/sequence/phoschem.htlm.
Sinha et al., "The preparation and application of functionalised synthetic oligonucleotides: III. Use of H-phosphonate derivatives of protected amino-hexanol and mercapto-propanol or-hexanol," *Nucleic Acids Research* 16(6):2659-2669 (1988).
Wilkinson, "Oligo Factory, A Profile of Automated Nucleic Acid Synthesizers," *The Scientist* 13(21):18 (1999) www.the-scientist.com/yr1999/oct/profile1_991025.html.
T. Maniatis et al., *Molecular Cloning*, Cold Spring Harbor Laboratory, 188-190 (1982).
R. J. Slater, "The Extraction and Fractionation of RNA," In: *Techniques in Molecular Biology*, J.M. Walker and W. Gaastra, eds., Macmillan, NY15, 113-120 (1983).
P. Chomczynski and N. Sacchi, "Single-step Method of RNA Isolation by Acid Guanidnium Thiocyanate-Phenol-Chloroform Extraction," *Anal. Biochem.* 162:156-159 (1987).
R.H. Alul et al., "Oxaly-CPG: A Labile Support For Synthesis of Sensitive Oligonucleotide Derivatives," *Nucleic Acids Res.*, 19(7):1527 (1991).
K.-P. Stengele and W. Pfleiderer, "Improved Synthesis of Oligodeoxyribonucleotides," *Tetrahed. Lett.*, 31(18):2549-2552 (1990).
B.S. Sproat and D.M. Brown, "A New Linkage For Solid Phase Synthesis of Oligodeoxyribonucleotides," *Nucleic Acids Res.* 13:8, 2979-2987 (1985).
Wallace et al., "Application of Synthetic Oligonucleotides to the Diagnosis of Human Genetic Diseases," *Biochimie* 67:755-762 (1985).
Studencki and Wallace, "Allele-Specific Hybridization Using Oligonucleotide Probes of Very High Specific Activity: Discrimination of the Human $\beta^U$- and $\beta^s$-Globin Genes," *DNA* 3(1): 7-15 (1984).

(Continued)

Primary Examiner—Celine Qian
(74) Attorney, Agent, or Firm—Medlen & Carroll, LLP

(57) ABSTRACT

A novel method for the labeling of oligonucleotides which results in the economical synthesis of 5' labeled molecules. A set of suitably protected and carefully selected set of amino linkers, a modified deprotination/cleavage protocol and standard coupling methodologies to are used to allow for the convergent synthesis of any number of labeled oligonucleotides.

2 Claims, 8 Drawing Sheets

OTHER PUBLICATIONS

Studencki et al., "Discrimination Among the Human $\beta^A$, $\beta^B$, and $\beta^C$-Globin Genes Using Allele-Specific Oligonucleotide Hybridization Probes," *American Journal of Human Genetics* 37:42-51 (1985).

Guide to Molecular Cloning Techniques, Ed. S.L. Berger and A.R. Kimmel, *Methods in Enzymology* 152:401 (1987).

G. Alvarado-Urbina et al., "Automated Synthesis of Gene Fragments," *Science* 214:270-274 (1981).

Operating Manual, "cDNA Synthesis and Cloning," Pharmacia Biotech (1994).

Catalog, "Nucleic Acid: purification, detection and labeling," Promega Corporation.

Catalog, "Oligotex-dT mRNA Kits," Qiagen Corporation.

Hansen and Braman, "Isolation of Pure RNA from Micro Amounts of Tissue or Cells in 30 Minutes," *Stratagen Cloning Systems*, 6:50.

Catalog, "Nucleic Acid Isolation and Purification," U.S.B., pp. 134-149.

Catalog, "Proteins & Genes," Novagen.

G.M. Bonora et al., "Structure of N-Tert-Butuyloxycarbonyl-D-leucyl-L-phenylalanylethanolamide," *J. Biol. Chem.* 258:14725-14732 (1983).

Sieber and Iselin, "Selective acidolytische Spaltung von Aralkyloxycarbonyl-Aminoschutzgruppen," *Helv. Chim. Acta* 51:614-622 (1968).

V.K. Prasad et al., "Solid-phase Reagents for the Isolation and Protection of Carbonyl Compounds," *J.Ster. Bioch.* 18:257-261 (1983).

Kanda et al., "New Potent Mitomycin Derivatives: Synthesis and Antitumor Activity of 7,7-(Ethylenedioxy)mitocins," *J. Med. Chem.* 35:2781-2786.

A. Pilc et al., "N-Ethoxycarbony-2-ethocy-1,2-dihydroquinoline, An Irreversible Receptor Inactivator, as a Tool for Measurement of $\alpha$-Adrenoceptor Occupancy In Vivo," *Eur. J. Pharm.* 212:109-111 (1992).

J.W. Lown et al. "Mechanism of Action of 2-Haloethylnitrosoureas on Deoxyribonucleic Acid," *Bioch. Pharm.* 34:1015-1024 (1985).

G.K. Watson et al., "Microbial Metabolism of the Pyridine Ring," *Biochem. J.* 146:157-172 (1975).

E. Palomino et al., "Synthesis and in Vitro Evaluation of Some Modified 4-Thiopyrimidine Nucleosides for Prevention or Reversal of AIDS-Associated Neurological Disorders," *J. Med. Chem.* 33:258-263 (1990).

Heikkila and Chattopadhyaya, "The 9-Fluorenylmethoxycarbonyl (Fmoc) Group for the Protection of Amino Functions of Cytidine, Adenosine, Guanosine and Their 2'-Deoxysugar Derivatives," *Acta Chem. Scand.* B37:263-265 (1983).

Webb and Matteucci, "Hybridization triggered cross-linking of deoxyoligonucleotides," *Nucleic Acids Research* 14(19):7661-7674 (1986).

Beaucage and Caruthers, "Deoxynucleoside Phosphoramidites-A New Class of Key Intermediates for Deoxypolynucleotide Synthesis," *Tetrahed. Lett.*, 22(20):1859-1862 (1981).

\* cited by examiner

Reaction 1

Reaction 2

Step 1

Step 2

COMPOSITIONS AND METHODS FOR LABELING OLIGONUCLEOTIDES

This is a Continuation-In-Part of application Ser. No. 09/344,226 filed on Jun. 25, 1999 now U.S. Pat. No. 6,750,357.

FIELD OF THE INVENTION

This invention generally relates to methods of labeling organic compounds for fluorescent detection. More particularly, the invention relates to the labeling of oligonucleotides with novel labels and the economical synthesis of labeled oligonucleotides.

BACKGROUND OF THE INVENTION

Currently, available technologies for the attachment of 5' end labels to synthetic oligonucleotides rely on two general approaches. The most popular approach requires the production of phosphoramidite derivatives of the desired label. In general, these phosphoramidites are of the structure L-LA-CEP where L is the desired label, LA is a linker arm and CEP is the protected phosphoramidite portion of the oligonucleotide molecule.

The resulting phosphoramidites are then coupled to the synthetic oligonucleotide via standard automated procedures. This process suffers from a number of disadvantages. First, the desired phosphoramidites are typically produced via multi-step, linear syntheses, making this a costly process. Second, phosphoramidites are compounds of limited stability resulting in significant losses when the compounds are purified and limited shelf life, particularly in solution.

The second approach is used in cases where no phosphoramidite is available or where the desired label is not compatible with standard DNA synthesis or deprotection methodologies. In this instance, a suitably protected linker arm phosphoramidite is attached via standard DNA synthesis procedures. Following cleavage and deprotection of the modified oligonucleotide, the label is added to the linker arm in a solution phase reaction. Typically this is accomplished via coupling of an activated ester form of the label to a terminal amine on the linker arm. As before, there are significant disadvantages to this approach. Solution phase chemistry is more labor intensive than traditional solid phase approaches making it more costly and resulting in lower yields. As with phosphoramidites, suitable activated labels must be synthesized or licensed. However, this approach has an advantage in that a common set of linker-CEPs can be utilized with a number of potential labels.

While existing technologies provide a way to synthesize oligonucleotides containing a number of standard labels for research purposes, what is lacking is a generalized procedure for the rapid production of oligonucleotides with novel labels and the economical synthesis of oligonucleotides with standard labels.

SUMMARY OF THE INVENTION

This invention generally relates to methods of labeling organic compounds for detection. More particularly, the invention relates to the labeling of oligonucleotides with novel labels and the economical synthesis of labeled oligonucleotides.

In one embodiment, the present invention contemplates the use of a suitably protected and carefully selected set of amine linkers, a modified deprotection/cleavage protocol and coupling methodologies to allow for the convergent synthesis of any number of labeled oligonucleotides.

In one embodiment, the present invention contemplates a method of labeling oligonucleotides, comprising: a) providing: i) a solid support-bound oligonucleotide comprising an amino group, ii) a bifunctional linker arm and iii) an activated label; b) reacting said solid support-bound oligonucleotide with said bifunctional linker arm to produce a support-bound linker-oligonucleotide, and; c) reacting said support-bound linker-oligonucleotide with said activated label to produce a labeled support-bound oligonucleotide. The present invention also contemplates that the bifunctional linker arm is selected from a group consisting of the compounds listed in Tables 1, 2 and 3. The present invention further contemplates that the activated label is selected from a group consisting of the compounds listed in Table 1, 2 and 3.

In another embodiment, the present invention contemplates a method of labeling oligonucleotides, comprising: a) providing: i) a solid support-bound oligonucleotide comprising an amino group, ii) a bifunctional linker arm and iii) an activated label; b) reacting said solid support-bound oligonucleotide with said bifunctional linker arm to produce a support-bound protected linker-oligonucleotide; c) deprotecting the amino group of said support-bound protected linker-oligonucleotide to produce a support-bound deprotected linker-oligonucleotide, and; d) reacting said support-bound deprotected linker-oligonucleotide with said activated label to produce a labeled support-bound protected oligonucleotide. The present invention also contemplates that the bifunctional linker arm is selected from a group consisting of the compounds listed in Tables 1, 2 and 3. The present invention further contemplates that the activated label is selected from a group consisting of the compounds listed in Table 1, 2 and 3.

In one embodiment, the present invention also contemplates the use of carboxyl linkers, phosphate linkers, etc.

DEFINITIONS

To facilitate understanding of the invention, a number of terms are defined below.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may have 5' and 3' ends.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refers to the annealing of a complementary sequence to the target nucleic acid. The ability of two polymers of nucleic acid containing complementary sequences to find each other and anneal through base pairing interaction is a well-recognized phenomenon. Marmur and Lane, Proc. Natl. Acad. Sci. USA 46:453 (1960) and Doty et al., Proc. Natl. Acad. Sci. USA 46:461 (1960). The terms "annealed" and "hybridized" are used interchangeably throughout, and are intended to encompass any specific and reproducible interaction between an oligonucleotide and a target nucleic acid, including binding of regions having only partial complementarity.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The stability of a nucleic acid duplex is measured by the melting temperature, or "$T_m$". The $T_m$ of a particular nucleic acid duplex under specified conditions is the temperature at which on average half of the base pairs have disassociated.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$-5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

As used herein, the term "purified" or "to purify" refers to the removal of some contaminants from a sample. The present invention contemplates purified compositions (discussed above).

As used herein, the term "partially purified" refers to the removal of a moderate portion of the contaminants of a sample to the extent that the substance of interest is recognizable by techniques known to those skilled in the art as accounting for a measurable amount of the mixture.

As used herein, the term "substantially purified" refers to the removal of a significant portion of the contaminants of a sample (e.g. >90%) to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are "functional" if they contain a binding region (i.e. a region having affinity for another molecule) and such binding can take place (i.e. the binding region functions, albeit with perhaps lower affinity than that observed for the full-length protein). Such "functional portions" of the gene product are typically greater than 10 amino acids in length, and more typically greater than 50 amino acids in length, and even more typically greater than 100 amino acids in length. "Functional portions" may also be "conserved portions" of the protein. The alignment of the various gene products permit one skilled in the art to select conserved portions of the protein (i.e. those portions in common between two or more species) as well as unconserved portions (i.e. those portions unique to two or more species). The present invention contemplates conserved portions 10 amino acids in length or greater, and more typically greater than 50 amino acids in length.

The present invention contemplates genes in operable combination with a promoter. "In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "nucleic acid sequence of interest" refers to any nucleic acid sequence the manipulation of which may be deemed desirable for any reason by one of ordinary skill in the art.

As used herein, the term "fusion protein" refers to a chimeric protein containing the protein of interest joined to an exogenous protein fragment. The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art.

As used herein, the term "bifunctional linker" and "bifunctional linker arm" refer to a compound that can link two additional compounds together by chemically interacting with both of them simultaneously. In the present invention, one example of a suitable linker is a phosphoramidite. In the present invention, for example, a bifunctional linker arm is where one functional group is suitable for coupling with the 5' hydroxyl group of an oligonucleotide and the second functional group is suitable for coupling with an available functionality on the label compound.

As used herein, the term "label" refers to chemical compounds that are capable of coupling with a linker-oligonucleotide of the present invention and are detectable by standard biochemical techniques (e.g., by light absorption, light emission, etc). Examples of labels used in the present invention include, carboxyl labels, isothiocyanate labels, sulfonyl chloride labels, amino labels and hydroxyl labels.

As used herein, the term "active label" refers to a label that is capable of reacting with another chemical. Such reactions may be, for example, coupling to another chemical. In the present invention, for example, the label is "activated" to allow for coupling with the linker-oligonucleotide.

As used herein, the term "protect" refers to the use of a chemical moiety to inhibit a reaction (for example, a coupling reaction) by blocking the reactive site on a compound.

As used herein, the term "deprotect" refers to the removal of a chemical moiety from a reactive site on a compound to allow the reactive site to, for example, couple to another compound.

As used herein, "solid support" refers to a non-liquid and non-gaseous substance to which chemical compounds such as oligonucleotides can attach to or be attached to. Gel substances and resins are considered to be solid supports in the context of the present invention. However, a variety of materials can be used, including but not limited to plastic, glass, silicon, metal and cellulose.

As used herein, "support-bound" refers to a compound that is bound to a solid support.

GENERAL DESCRIPTION OF THE INVENTION

Figure 1A:
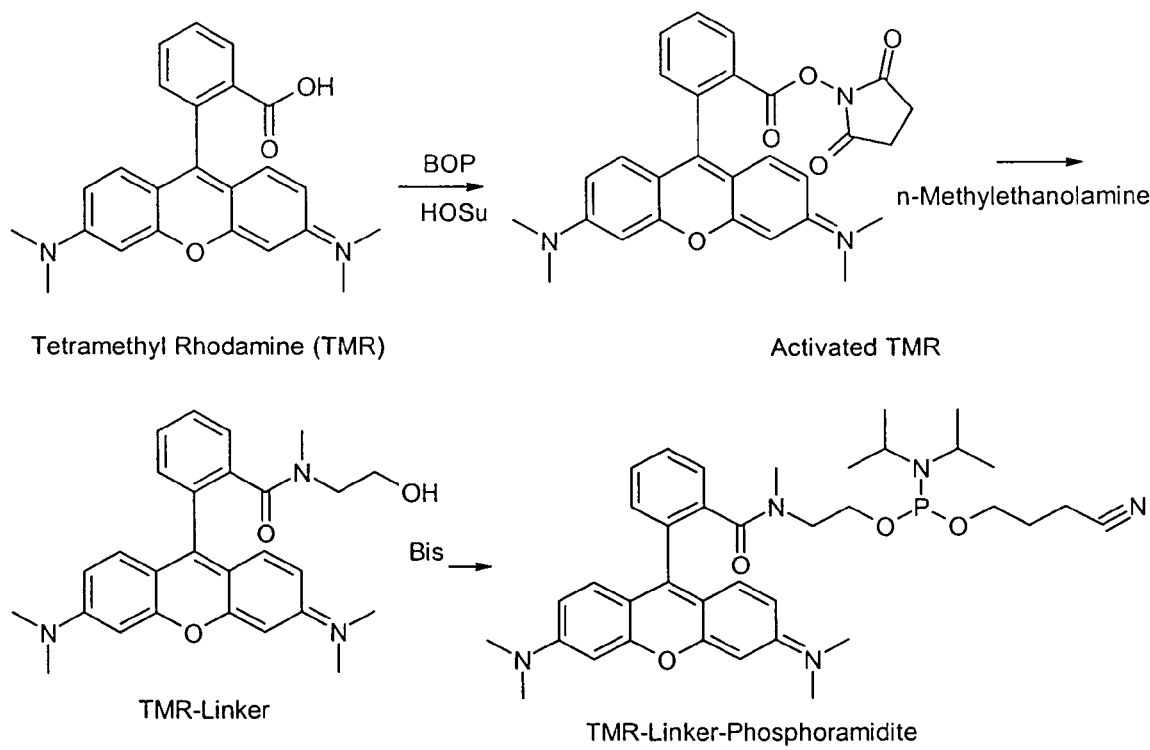
FIG. 1A shows one embodiment of a method for production of phosphoramidite.

This invention generally relates to methods of labeling organic compounds for fluorescent detection. More particularly, the invention relates to the labeling of oligonucleotides with novel labels and the economical synthesis of labeled oligonucleotides.

Current automated DNA sequencing methods make use of multiple fluorescent labels for concurrent detection of base sequence in a single gel lane or capillary. Many of the commonly used fluorescent dues for sequencing are produced as a mixture of isomers, including those of the rhodamine family. (In reference to rhodamine dyes, we will use the numbering scheme described in the Color Index by the Association of Textile Chemists, 2nd Edition, 1971). Single isomer due labels are preferred for high resolution techniques such as DNA sequencing and capillary electrophoresis, because slight differences in spectral properties exist between different isomeric forms of the fluorophores. In addition, differences in the electrophoretic mobilities of 5- and 6-isomer fluorophore-tagged primers (e.g., 5- and 6-carboxytetramethylrhodamine) can lead to band broadening if mixtures of isomers are used (Hung et al., *Analytical Biochem.*, 238, 165–170, 1996). Therefore, single isomer forms must be purified before preparing fluorescent dye labeling reagents intended for use in labeling oligonucleotides for DNA sequencing.

Some fluorescent dye labels can be attached to the 5' end of oligonucleotides during the process of synthesizing the primers (e.g., fluorescein using a fluorescein phosphoramidite reagent). These dye phosphoramidites react properly under phosphite chemistry conditions because protection of the two active oxygen groups on the fluorescein moiety prevent possible side reactions between the phosphoramidite and fluorescein. In addition, modification with the protecting groups holds the 3-position carboxylic acid function in the closed ring lactone form, preventing proton donation from the carboxylate to the N,N-diisophropylamino phosphoramidite. Protonation will convert the diisopropylamino moiety into a good leaving group, which could decompose the reagent. Some rhodamine phosphoramidites synthesized (for example, U.S. Pat. No. 5,231,191, issued Jul. 27, 1993 to Woo et al.) have the 3-position carboxylic acid function existing in equilibrium between the closed (lactose) and open (acid) form. When the reagent is used in oligonucleotide synthesis, the "acidic" environment will favor formation of the carboxylate-onium cation form. Proton donation from the carboxylic acid moiety to the N,N-diisopropylamino could occur and result in reagent instability, compromising oligonucleotide labeling efficiency.

Some fluorescent dye labels (e.g., fluorescein and related derivatives) retain their fluorescent properties during cleavage of the labeled oligonucleotide from the solid phase support and removal of protecting groups with concentrated aqueous ammonia, the standard method in current practice. However, dyes in the rhodamine family are susceptible to chemical modification by the ammonia treatment, which drastically decreases their fluorescent properties. Thus, it is a general practice for rhodamine-type dyes to be attached to the 5' end of oligonucleotides which have been modified with linker functionalities (e.g., primary amine) after automated synthesis, cleavage and deprotination. This dye labeling requires additional steps and manual labor, incurring greater cost inconvenience in the overall synthesis of 5'-rhodamine dye-labeled oligonucleotides.

Currently available technologies for the attachment of 5' end labels to synthetic oligonucleotides rely on two general approaches. The most popular approach requires of the production of phosphoramidite derivatives of the desired label and subsequent coupling to a support-bound protected oligonucleotide via standard oligonucleotide synthesis techniques. This process is exemplified in FIGS. 1A and 1B, which shows the synthesis of a tetramethylrhodamine (TMR) labeled oligonucleotide.

FIG. 1A details the production of the phosphoramidite. Following the activation of the carboxyl functional group, the tetramethylrhodamine is reacted with a bifunctional linker arm, in this case N-methylaminoethanol. Such a linker arm serves several functions. It provides needed distance between the label and the oligonucleotide, a functional group, in this case an amine; appropriate for reaction with the tetramethylrhodamine and a functional group, in this case a hydroxyl, which will ultimately allow for the coupling to the 5' hydroxyl of a support-bound protected oligonucleotide. Following the attachment of the linker arm to the rhodamine, the terminal hydroxyl is activated toward coupling with the oligonucleotide by conversion into the phosphoramidite.

Figure 1B:
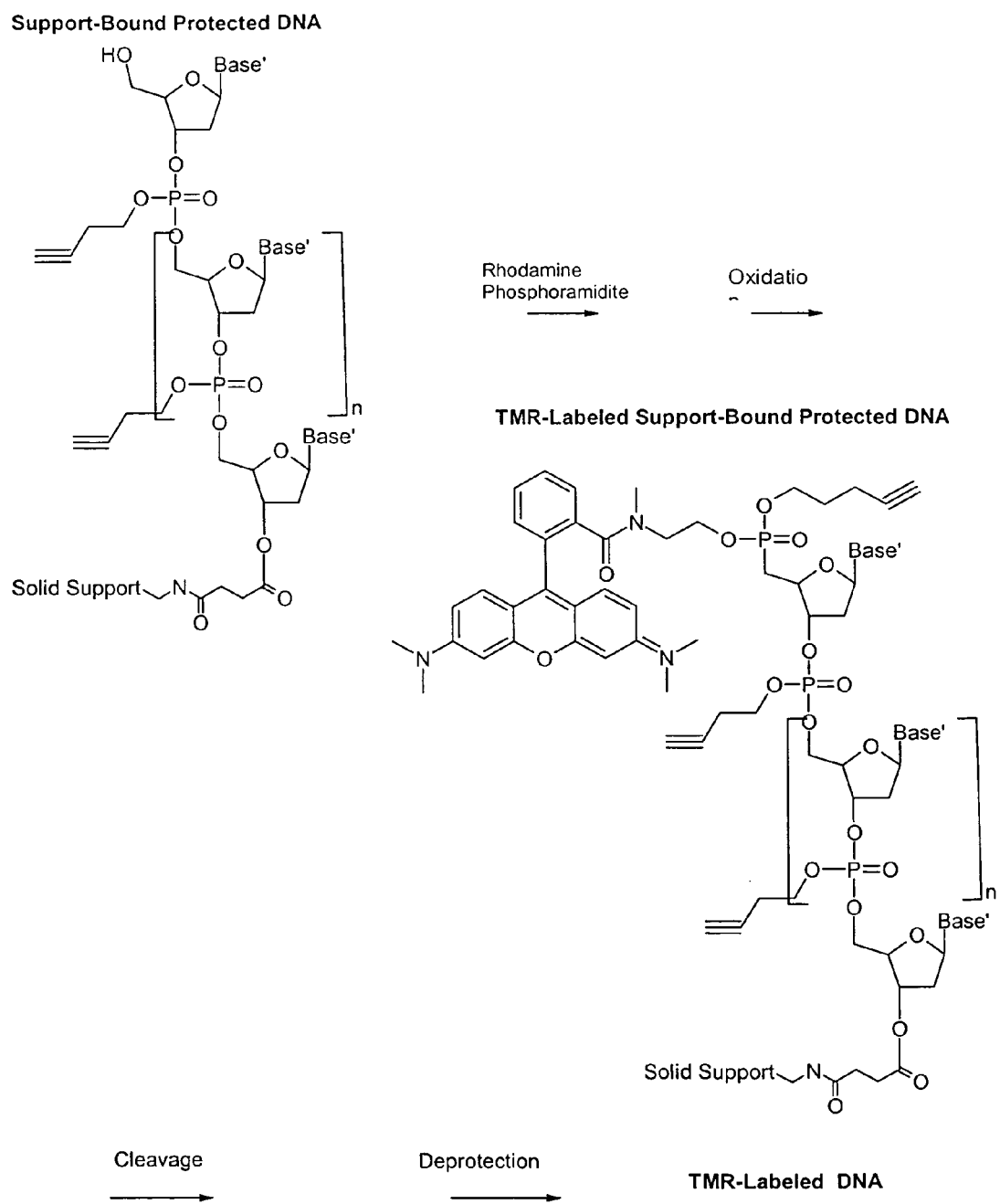
FIG. 1B shows one embodiment for the reaction of a phosphoramidite with an oligonucleotide.
Figure 2A:
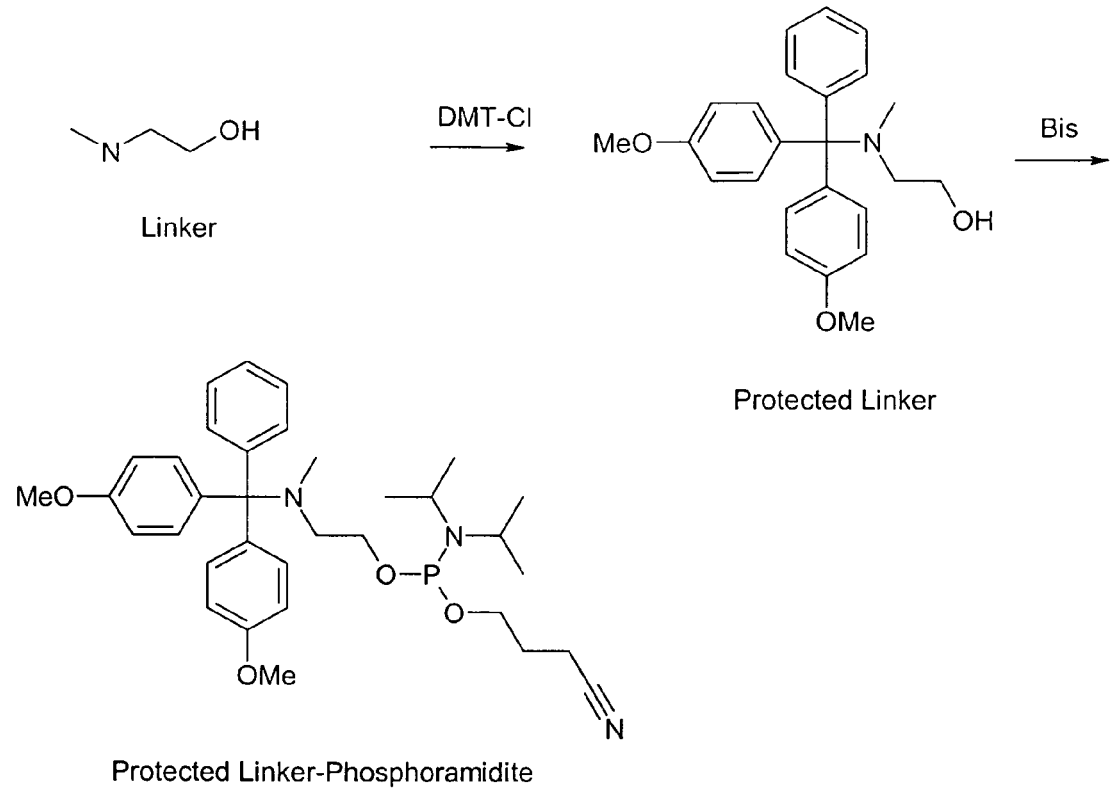
FIG. 2A shows one embodiment for the synthesis of a protected linker-phosphoramidite and an activated tetramethylrhodamine.
Figure 2A:
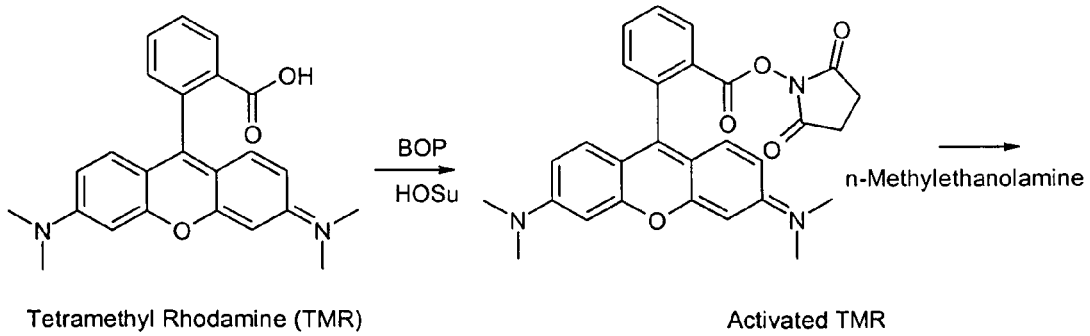

Reaction of the phosphoramidite produced in FIG. 1A with an oligonucleotide is detailed in FIG. 1B. Following a standard oligonucleotide synthesis, the support-bound oligonucleotide is 5' deprotected in preparation for another synthesis cycle. In this case, rhodamine phosphoramidite is substituted for the nucleoside phosphoramidite and coupled as usual for DNA synthesis. Following oxidation, the support-bound labeled oligonucleotide is cleaved from the support and fully deprotected to yield the final product A two-step variation of this approach is used only in cases where the corresponding phosphoramidite is not available. This approach is exemplified in FIGS. 2A and 2B, which illustrate the approach using TMR as the labeling compound. While ultimately producing the same product as the TMR Phosphoramidite, this approach segregates the process into two distinct coupling processes. FIG. 2A details the synthesis of the reagents required for this process. Reaction 1 shows the production of a linker phosphoramidite with the same base linker molecule use above. In this case, the amino group of the N-methylaminoethanol is first protected as the dimethoxytrityl derivative. In a second reaction, the hydroxyl group is then activated toward coupling with the oligonucleotide by conversion into the phosphoramidite. Reaction 2 shows the production of an activated TMR that will be use in the second part of the coupling scheme.

Figure 2B:
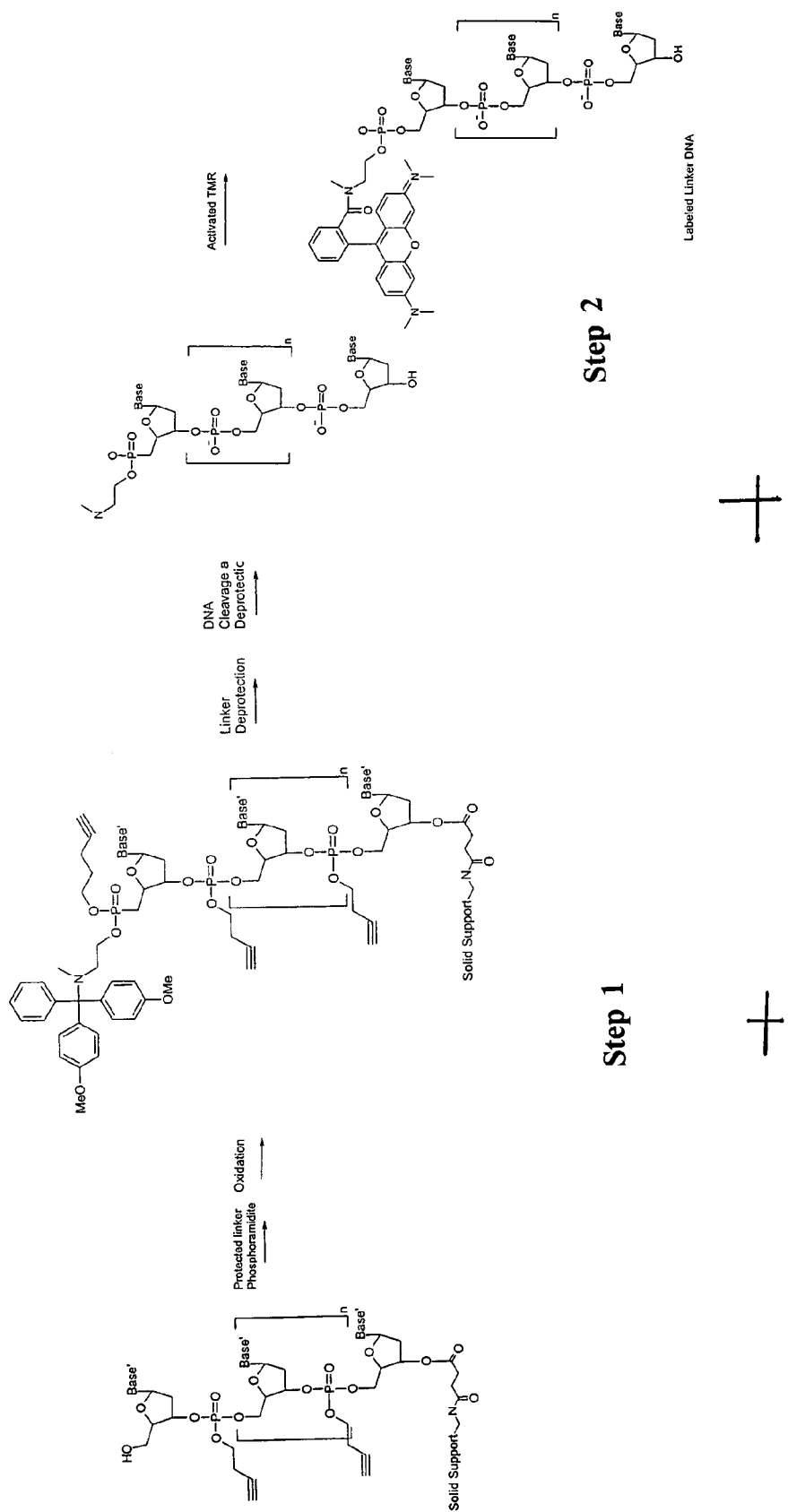
FIG. 2B shows one embodiment for the attachment of a linker phosphoramidite to an activate label.

The sequential attachment of linker phosphoramidite and activated label is detailed in FIG. 2B. In a preliminary step, the linker phosphoramidite is attached to the 5' hydroxyl of a support-bound fully protected oligonucleotide via standard DNA synthesis procedures. Following the removal of the amino protecting group, the oligonucleotide is cleaved from the solid supports and deprotected yielding a linker-modified oligonucleotide. This product is then reacted in solution with activated label to yield labeled oligonucleotide.

DESCRIPTION OF PREFERRED EMBODIMENTS

The present invention is not limited to any particular mechanism and the descriptions contained herein are for illustrative purposes only.

Figure 3:
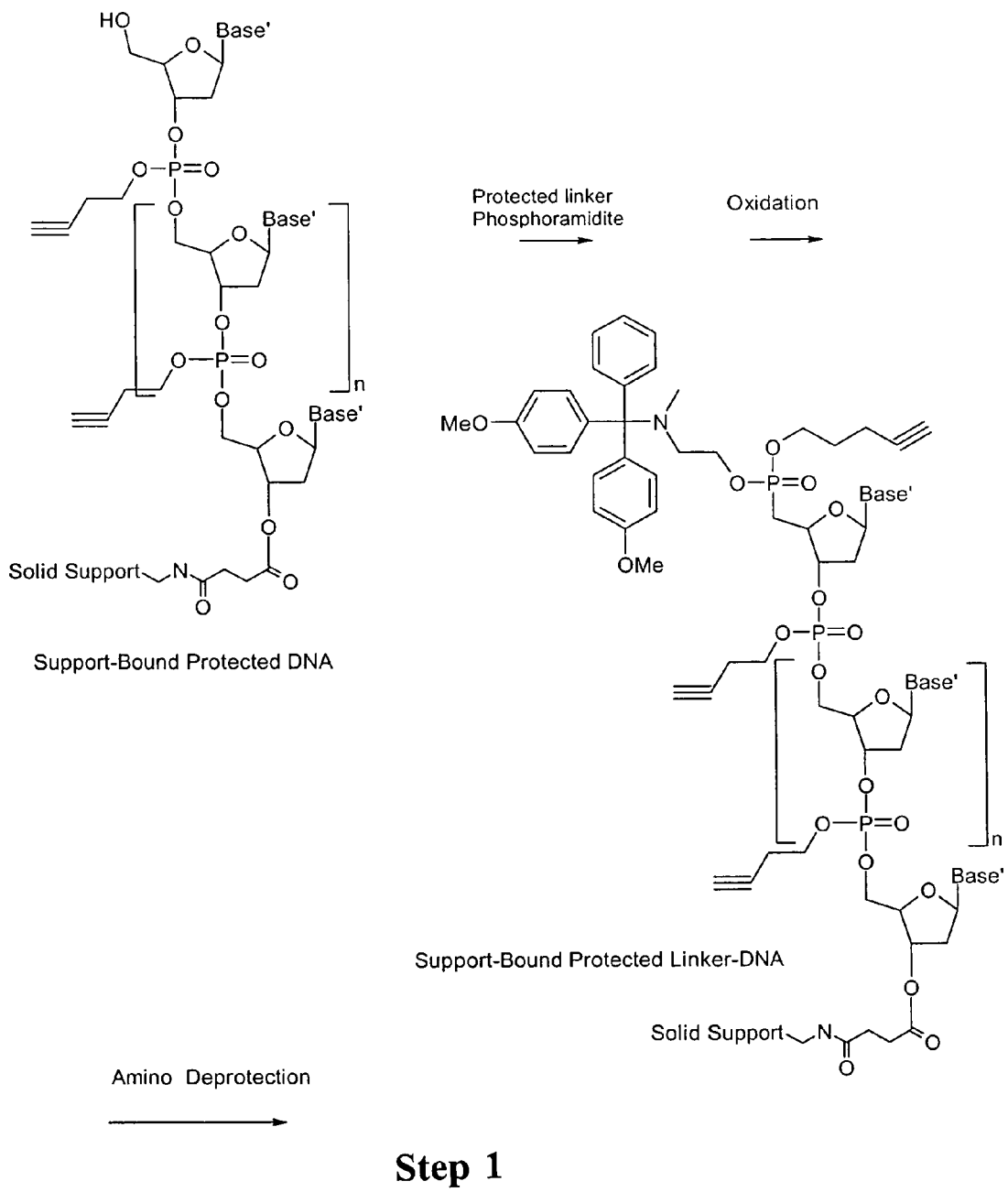
FIG. 3 shows one embodiment for the production of a tetramethylrhodamine-labeled oligonucleotide as practiced in the present invention.
Figure 3:
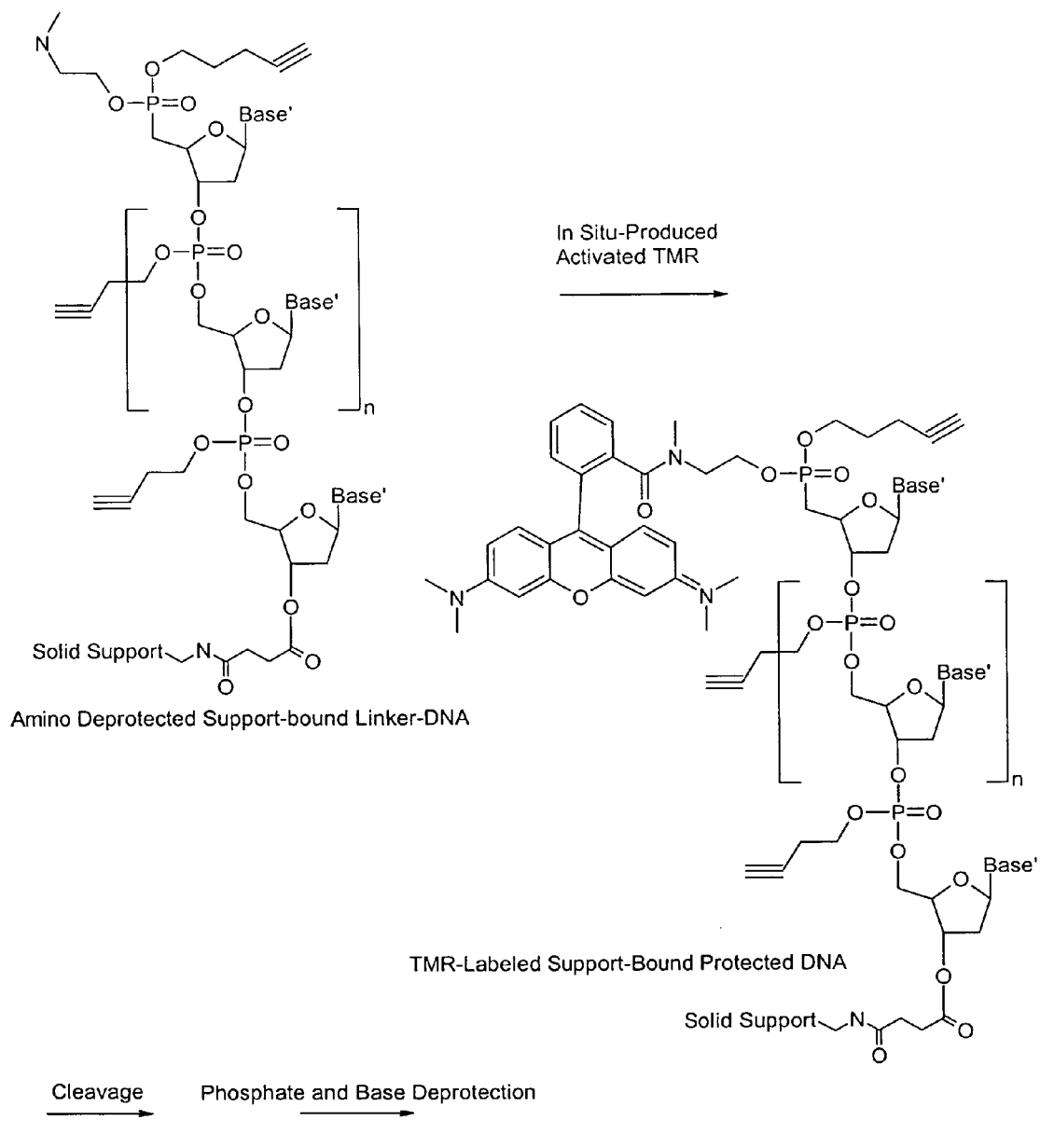

Preparation of a TMR-labeled oligonucleotide as practiced in the current invention is detailed in FIG. 3. Conceptually, the approach consists of a novel and empirically discovered modification of the less popular two step procedure such that both reactions are conducted on the solid phase support. In Step 1, the fully protected support-bound oligonucleotide is reacted with linker phosphoramidite and the amino group is deprotected. In Step 2, the product is reacted with activated TMR, which has been produced in situ prior to addition. Cleavage and deprotection yield the desired oligonucleotide.

This approach, while simple in concept, exhibits a number of significant advantages over the traditional approaches to DNA labeling. As compared to the 1 step phosphoramidite procedure, the current method results in exceptional cost savings and/or labor savings for those engaged in the production of a large variety of labeled oligonucleotides. On a molar basis, the combined cost of the linker phosphoramidite and the basic labeling compound ranges from 10–30% of the cost of a fully prepared label phosphoramidite. In practice, further cost reductions are realized when one considers the instability of phosphoramidites in solution. Commercially available label solid phosphoramidites are packaged in amounts sufficient for 10 or more labeling reactions. Once placed in solution, any unused material would have a useful life less than one week. Use of a common linker phosphoramidite with a variety of labeling compound would greatly reduce such waste in a typical production environment.

Further advantages are realized when one considers the required labor and the chemical difficulties in producing new label phosphoramidites and the need to provide a variety of linker arms each of which is specific for certain applications. Apart from the labor required for preparation, the production of new label phosphoramidites is often hindered by the inherent instability of a phosphoramidite and the poor solubility and/or purification properties of many dye compounds that one might consider as a labeling agent. Thus the poor physical properties of the label often makes it difficult to isolate pure label intermediates and even more difficult to isolate active phosphoramidite without significant losses due to amidite decomposition. It is, therefore, desirable to restrict the phosphoramidite synthesis to a few well-define linkers and to minimize number of reactions one attempts with basic labeling compounds. In many of the examples cited below, labeled oligonucleotides were synthesized by our novel method using commercially available linker and label.

While the traditional two-step procedure also addresses the disadvantages of the 1 step phosphoramidite, the current invention provides for additional, unanticipated improvements. As a totally solid phase system, it is easily automated on conventional DNA synthesizers (e.g., the Eppendorf D200 automated synthesizer; the Amersham Pharmacia OligoPilot II; the PE Biosystem ABI 3948 and Expedite 8909). All the reactions described below can be carried out on a conventional synthesizer by a simple user-define couple protocol. Additionally, the solid phase protocol also overcomes certain chemical limitations imposed by the solution phase second step of the traditional procedure. In the traditional procedure, this step is carried out in aqueous solution where many labeling compounds of interested have limited solubility and/or stability. No such limitations occur in the solid phase where reactions can take place at higher concentrations in solvents more compatible with the labeling reagent. This results in more complete reaction and a larger set of potential labeling reagents. Further advantages are realized in subsequent purification steps as any excess labeling reagent is simply removed by washing the support-bound oligonucleotide prior to cleavage and deprotection.

EXPERIMENTAL

Example 1

Although not limited to any particular mechanism, in general terms, the process of the current invention consists of a two step, solid-phase reaction. In the first step, a support-bound, fully-protected oligonucleotide is reacted with bifunctional linker arm where one functional group is suitable for coupling with the 5' hydroxyl group of the oligonucleotide and the second functional group is suitable for coupling with an available functionality on the label compound. If required for chemical compatibility, the second functional group may bear a removable protecting group. After removal any protecting groups, the second functional groups is then coupled with a labeling compound to produced a labeled oligonucleotide. While it is preferred in some situations to use a carboxyl containing label and a linker that consist of a phosphoramidite for coupling to the oligonucleotide and a protected amine for coupling to the label (see, for example, FIG. 3), other functional groups are compatible with the process. The following examples are meant to illustrate variations on this theme.

Oligonucleotide Synthesis

All oligonucleotide synthesis was carried out on an Eppendorf D200 automated synthesizer. Manufacturer's standard coupling protocols were followed for DNA synthesis and 5' addition of amino linker. Synthesis scales were 0.2 to 1 µmole.

Carboxyl Labels/Protected Amine Phosphoramidites

Variations on the theme of coupling carboxyl substituted label to an amino/phosphoramidite linker were conducted with eleven labeling compounds and two linker phosphoramidites. All labeling reactions were carried out in dry DMF/10% triethylamine at a label concentration of 0.2 M and a BOP concentration of 0.22 M. Coupling was effected by exposing the solid support to 50 µl of the coupling mixture for 1 hour at ambient temperature. Free label was removed by repeated washing with DMF followed by acetonitrile. Labeled oligo was cleaved from the solid support by exposure to 0.4 M NAOH in 4:1 methanol/water for 16 hours at 27 degrees C. Labeled oligo was isolated by standard gel filtration techniques. Reactions with FAM were most successful if standard isobutyryl protection was used for the phenolic oxygens. Variations in the label and/or linker phosphoramidite are shown in the following table. (See, Table 1 next two pages).

TABLE 1
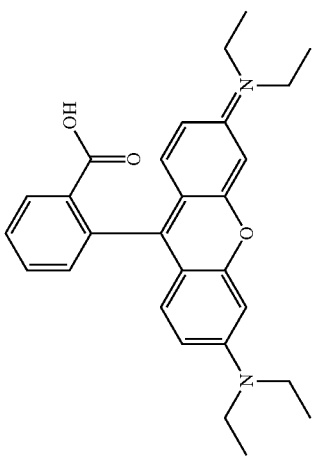

TABLE 1-continued

| Label | Linker | Product |
|---|---|---|
| Tetramethylrhodamine (structure) | (structure) | (structure) |
| Tamara (structure) | (structure) | (structure) |

TABLE 1-continued

| Label | Linker | Product |
|---|---|---|
| Fam | (structure) | (structure) |
| Diisobutyryl Fam | (structure) | (structure) |

TABLE 1-continued

| Label | Linker | Product |
|---|---|---|
| Pyrenebutyric acid | (structure) | (structure) |
| 3-Carboxycoumarin | (structure) | (structure) |

TABLE 1-continued

| Label | Linker | Product |
|---|---|---|

TABLE 1-continued

| Label | Linker | Product |
|---|---|---|

Example 2

In the following set of experiments the versatility of the solid phase approach is illustrated by the use of other amine-reactive labels, isothiocynates and sulfonyl chlorides with the amino/phosphoramidite linker. This is a three-step process where the amino group of the linker arm is first reacted with succinic anhydride and then reacted with an amino label and an example of a hydroxyl label coupled via a bisphosphoramidite.

Isothiocyanate Labels

Reactions were carried out in dry DMF/10% triethylamine at a label concentration of 0.2 M. Coupling was affected by exposing the solid support to 50 µl of the coupling mixture for 1 hour at ambient temperature. Free label was removed by repeated washing with DMF followed by acetonitrile. Labeled oligo was cleaved from the solid support by exposure to 0.4 M NAOH in 4:1 methanol/water for 16 hours at 27 degrees C. Labeled oligo was isolated by standard gel filtration techniques.

TABLE 2
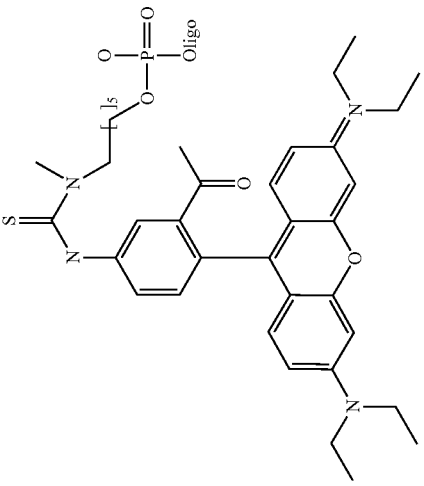

Sulfonyl Chloride Labels

All reactions were carried out in dry DMF/10% triethylamine at a label concentration of 0.2 M. Labels containing sulfonic acids functional groups were converted to the sulfonyl chloride in a separate reaction prior to coupling. Coupling was affected by exposing the solid support to 50 µl of the coupling mixture for 1 hour at ambient temperature. Free label was removed by repeated washing with DMF followed by acetonitrile. Labeled oligo was cleaved from the solid support by exposure to 0.4 M NAOH in 4:1 methanol/water for 16 hours at 27 degrees C. Labeled oligo was isolated by standard gel filtration techniques.

TABLE 3

| Label | Linker | Product |
|---|---|---|
| Sulforhodamine B Acid Chloride | | |
| Pyrenetrisulfonylchloride | | |

Amino Labels

Figure 4:
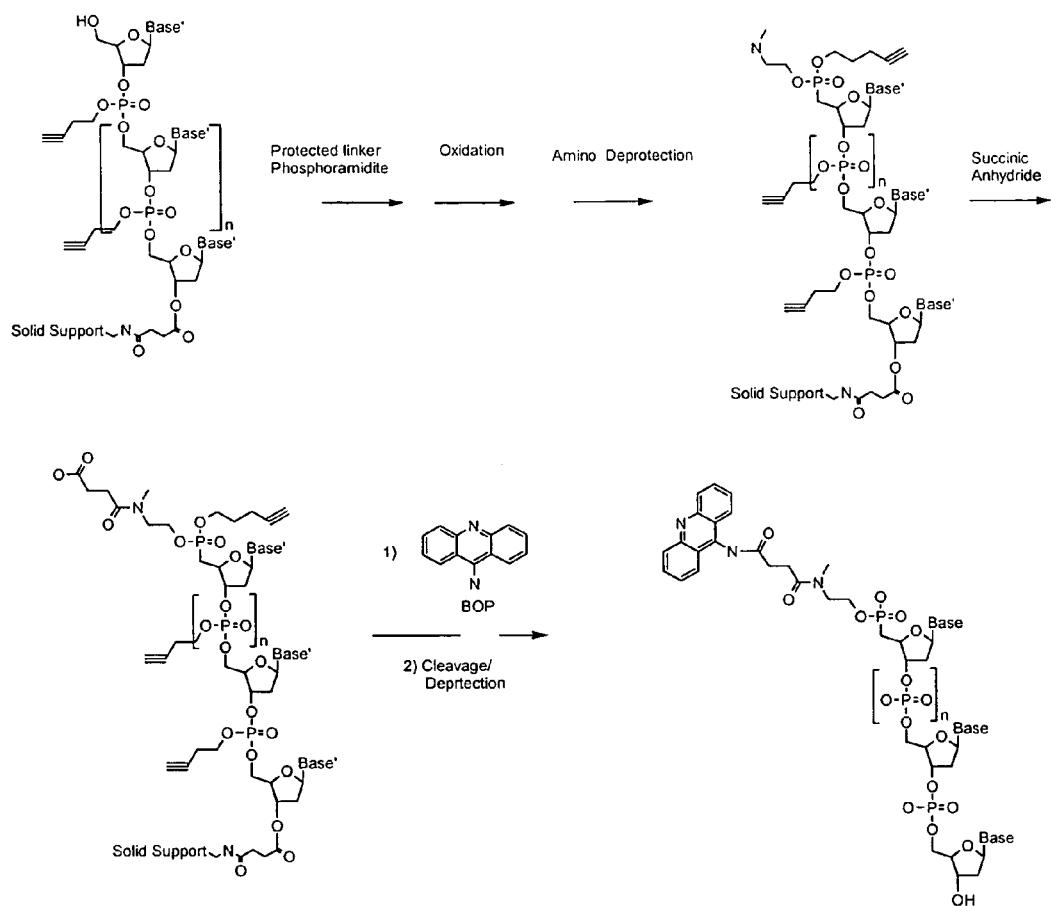
FIG. 4 shows one embodiment for the synthesis of an amino labeled oligonucleotide as practiced in the present invention.

In this experiment, the amino group of the amino functionality was first derivatized with succinic anhydride to provide a carboxy functional group which, in turn, was reacted with the amino group on a labeling compound (FIG. 4).

Figure 5:
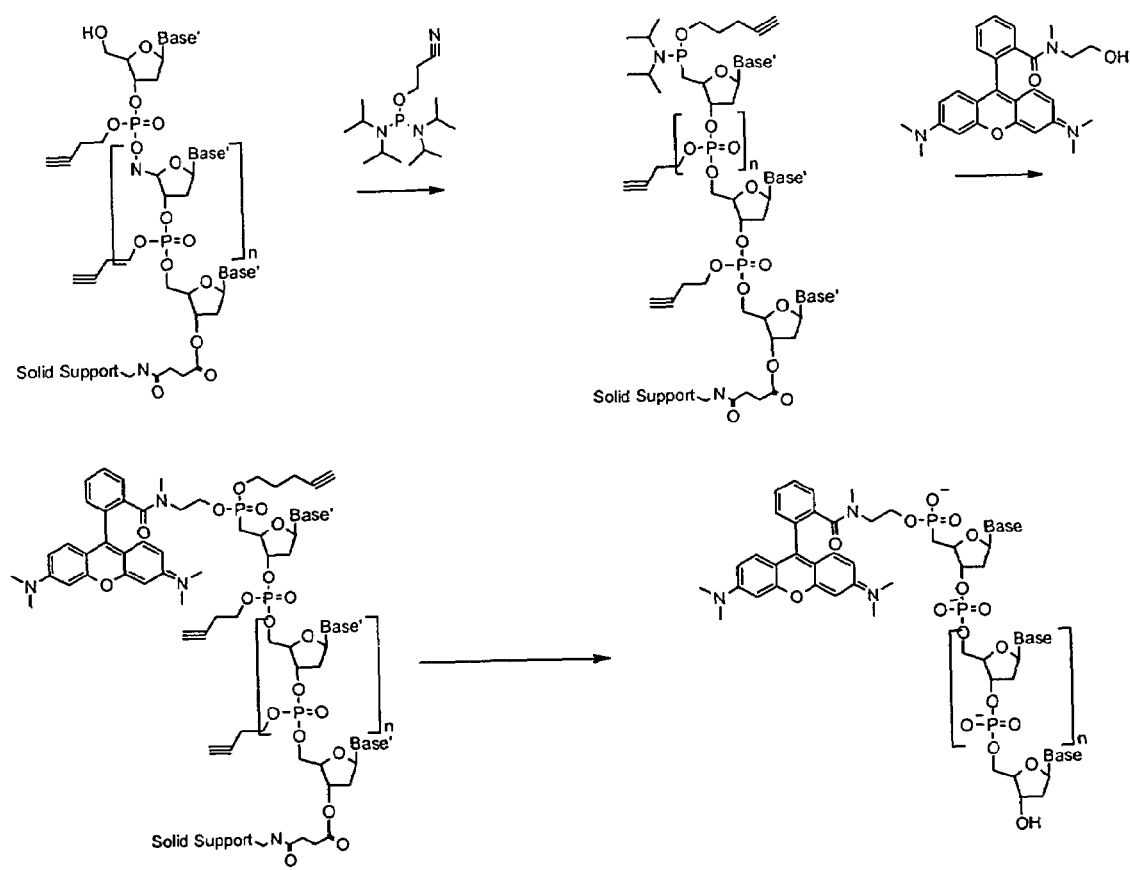
FIG. 5 shows one embodiment for the synthesis of a hydroxyl labeled oligonucleotide as practiced in the present invention.

The amino-modified support-bound oligo was reacted for 10 minutes with a 50:50 mixture of 8:1:1 THF:Pyridine:Succinic anhydride and 9:2 Pyridine:N-methylimidazole. The solid support was washed with acetonitrile prior to coupling. Coupling was carried out in dry DMF/10% triethylamine at a label concentration of 0.2 M and a BOP concentration of 0.22 M. Coupling was affected by exposing the solid support to 50 µl of the coupling mixture for 1 hour at ambient temperature. Free label was removed by repeated washing with DMF followed by acetonitrile. Labeled oligo was cleaved from the solid support by exposure to 0.4 M NaOH in 4:1 methanol/water for 16 hours at 27 degrees C. Labeled oligo was isolated by standard gel filtration techniques Hydroxyl Labels In the following example, the bifunctional linker is bisphosphoramidite capable of reaction with two hydroxyls groups. In the first reaction the phosphoramidite is reacted with the 5' hydroxyl of a fully protected, support bound oligonucleotide. The resulting compound is the reacted with a rhodamine derivative bearing a free hydroxyl to yield the desired product (FIG. 5).

As a test compound, Rhodamine B was reacted with N-methylamino ethanol to form an amide derivative containing a free hydroxyl. Unmodified, support-bound oligo was reacted with a 0.2 M Bisphosphite/0.1 M Tetrazole solution in acetonitrile for 5 minutes at ambient temperature. The solid support was washed with acetonitrile and exposed to a 0.2 M solution of label in dry DMF for 5 minutes at ambient temperature. Free label was removed by repeated washing with DMF followed by acetonitrile. Labeled oligo was cleaved from the solid support by exposure to 0.4 M NaOH in 4:1 methanol/water for 16 hours at 27 degrees C. The labeled oligo was isolated by standard gel filtration techniques.

From the foregoing it should be clear that the present invention provides novel methods for the economical synthesis of oligonucleotides with novel labels.

What is claimed is:

1. A method of labeling oligonucleotides, comprising:
   a) providing:
      i) a solid support-bound oligonucleotide comprising an amino group;
      ii) a bifunctional linker selected from the group consisting of:

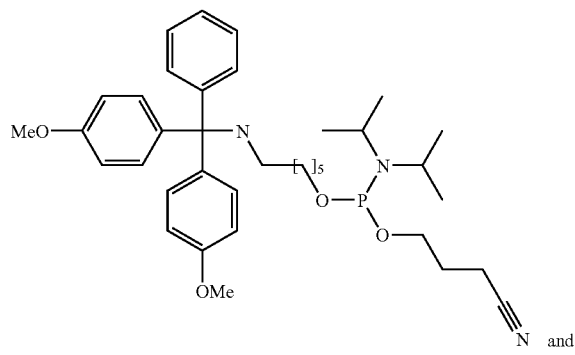

and

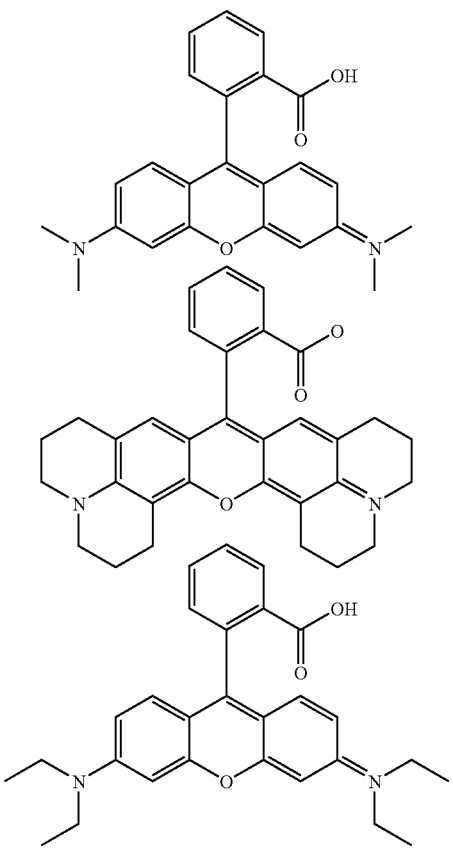

iii) an in situ unactivated label selected from the group consisting of:

b) reacting said solid support-bound oligonucleotide with said bifunctional linker arm to produce a support-bound, linker-oligonucleotide;
c) reacting said in situ unactivated label to create an in situ activated label; and
d) reacting said support-bound linker-oligonucleotide with said activated label to produce a labeled support-bound protected oligonucleotide.

2. A method of labeling oligonucleotides, comprising:
   a) providing:
      i) a solid support-bound oligonucleotide comprising an amino group;
      ii) a bifunctional linker arm selected from the group consisting of:

iii) an in situ unactivated label selected from the group consisting of:

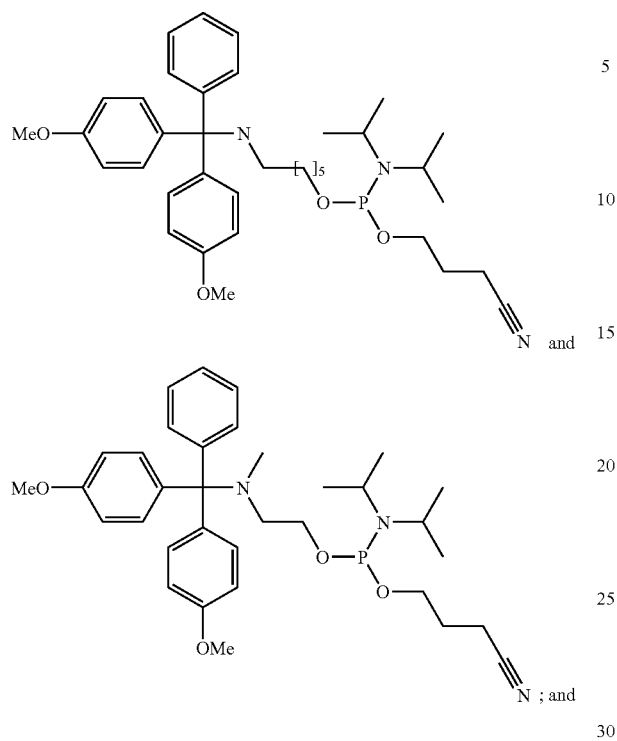

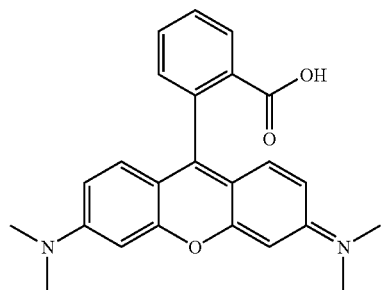

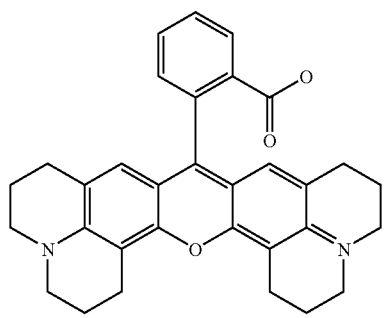

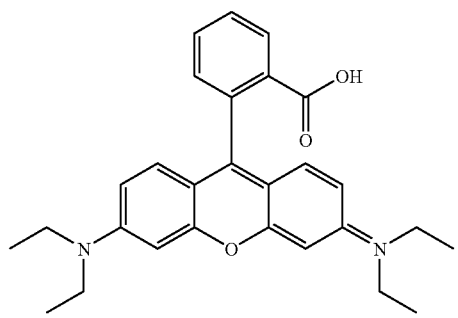

b) reacting said solid support-bound oligonucleotide with said bifunctional linker arm to produce a support-bound, linker-oligonucleotide;

c) reacting said in situ unactivated label to create an in situ activated label;

d) deprotecting the amino group of said support-bound, protected linker-oligonucleotide to produce a support-bound deprotected linker-oligonucleotide, and;

e) reacting said support-bound deprotected linker-oligonucleotide with said activated label to produce a labeled support-bound protected oligonucleotide.

* * * * *